US006814981B1

(12) United States Patent
Cox et al.

(10) Patent No.: US 6,814,981 B1
(45) Date of Patent: Nov. 9, 2004

(54) GANGLIOSIDE IMMUNOSTIMULATING COMPLEXES AND USES THEREOF

(75) Inventors: John Cooper Cox, Victoria (AU); Bengt John Lennart Ronnberg, Uppsala (SE); Sigrid Elisabet Sjolander, Harmanger (SE)

(73) Assignee: CSL Limited, Victoria (AU)

( * ) Notice: Subject to any disclaimer, the term of this patent is extended or adjusted under 35 U.S.C. 154(b) by 0 days.

(21) Appl. No.: 09/445,749
(22) PCT Filed: Jun. 12, 1998
(86) PCT No.: PCT/AU98/00453
§ 371 (c)(1),
(2), (4) Date: Feb. 10, 2000
(87) PCT Pub. No.: WO98/56420
PCT Pub. Date: Dec. 17, 1998

(30) Foreign Application Priority Data

Jun. 12, 1997 (AU) .............................. PO 7329

(51) Int. Cl.⁷ ................................................ A61K 9/51
(52) U.S. Cl. ................. 424/499; 424/210.1; 424/193.1; 424/277.1; 424/489; 424/484
(58) Field of Search .............................. 424/400, 206.1, 424/210.1, 277.1, 280.1, 283.1, 484, 497, 489, 499; 514/2, 15

(56) References Cited

U.S. PATENT DOCUMENTS

| 5,464,630 A | 11/1995 | Six et al. ..................... 424/450 |
| 5,807,559 A | * 9/1998 | Jondal ..................... 424/278.1 |
| 6,218,166 B1 | * 4/2001 | Ravindranath et al. ..... 435/366 |

FOREIGN PATENT DOCUMENTS

| AU | 20103/83 | 5/1984 |
| EP | 0 180 564 | 10/1985 |
| WO | 90/03184 | 4/1990 |
| WO | 94/16731 | 8/1994 |

OTHER PUBLICATIONS

Barr IG, et al. Immunology and Cell Biology. 1996; 74: 8–25.*
Gaugler B, et al. J Exp Med. Mar. 1, 1994; 179 (3): 921–30.*
Livingston, PO, 1995, Immunological Reviews, vol. 145, pp. 146–166.*

Osband, Me and Susan Ross, 1990, Immunology Today, vol. 11 (6), 193–195.*
Bocchia M, et al. Haematologica 2000; 85: 1172–1206.*
Bengtsson K, et al. Vaccine Jun. 1996; 14 (8): 753–760.*
Ritter G, et al. Int J Cancer 1995; 62: 668–672.*
Cox J, et al. BioDrugs Dec. 1999; 12 (6): 439–453.*
Ezzel C. J NIH Res Jan. 1995; 7: 46–49.*
Mukherji B, et al. Proc. Natl Acad Sci USA Aug. 1995; 92: 8078–8082.*
Jaeger E, et al. Int J Cancer 1996; 66: 162–169.*
Boon T. Adv Cancer Res 1992; 58: 177–210.*
Arceci RJ. J Mol Med 1998; 76: 80–93.*
Lee K–H, et al. J Immunol 1999; 163: 6292–6300.*
Zaks TZ, et al. Cancer Res Nov. 1, 1998; 58: 4902–4908.*
Gura T. Science Nov. 7, 1997; 278: 1041–1042.*
Bodey B, et al. Anticancer Res 2000; 20: 2665–2676.*
Yamshchikov G, et al. Clin Cancer Res Mar. 2001; 7 (Suppl): 909s–916s.*
Spitler LE. Cancer Biother 1995; 10 (1): 1–3.*
Cox AL, et al. Science Apr. 29, 1994; 264: 716–719.*
Hu X, et al. Cancer Res Jun. 1, 1996; 56: 2479–2483.*
Gao P, et al. J Immunother 2000; 23 (6): 643–653.*
Cox et al., "animal parasite control utilizing biotechnology", Adv. Adj. Tech. and App., 4:49–112, 1992.
Helling et al, "Ganglioside conjugate vaccines" Mol. Chem. Nuero., vol. 21, 21:299–309, 1994.
Sen et al., "prelinical evaluation in nonhuman primates of murine monoclonal anti–idiotype that mimics the Disialoganglioside GD2¹", Clinical Cancer Resrch, 3:1969–1976, 1997.

* cited by examiner

Primary Examiner—Yvonne Eyler
Assistant Examiner—Stephen L. Rawlings
(74) Attorney, Agent, or Firm—Foley & Lardner LLP

(57) ABSTRACT

An immunostimulating complex comprising one or more gangliosides, illustrated by the ganglosides GM2, GD2, GD3 or GT3, is useful as a prophylactic or therapeutic agent in the treatment of tumors, inter alia, especially melanomas.

10 Claims, 7 Drawing Sheets

GANGLIOSIDE IMMUNOSTIMULATING COMPLEXES AND USES THEREOF

This application is the national phase of PCT/AU98/00453, filed Jun. 12, 1998, and claims priority, under 35 U.S.C. § 119, to Australian provisional application No. PO7329/97, filed Jun. 12, 1997.

The present invention relates generally to an immunostimulating complex comprising one or more gangliosides and more particularly to an immunostimulating complex comprising at least one of the gangliosides GM2, GD2, GD3 or GT3. The present invention is useful, inter alia, as a prophylactic and/or therapeutic agent in the treatment of tumours, and more particularly, melanomas.

The bibliographic details of the publications referred to by author in this specification are collected at the end of the description.

Throughout the specification, unless the context requires otherwise, the word "comprise" or variations such as "comprises" or "comprising", will be understood to imply the inclusion of a stated element or integer or group of elements or integers but not the exclusion of any other element or integer or group of element or integer.

The incidence of malignant melanoma has been increasing rapidly over the last ten years with the survival rate of patients diagnosed with melanoma decreasing with increasing primary tumour thickness (Batch et al., 1982). Patients with regional lymphnode metastasis generally have a five year survival rate of less than 35% following dissection (Coit et al., 1991).

The identification of tumour associated antigens has provided further scope for tumour related therapies. Tumour antigens, both those which are unique to tumour cells and those which are shared with normal cells, have emerged as potential targets for active immunisation. One example of a class of tumour antigens are the gangliosides. Gangliosides are sialated glycosphingolipids consisting of hydrophilic (sugar) and hydrophobic (ceramide) portion. They are prevalent in brain and other neural crest derived cells and are also found on the tumours originating from these cells— astrocytomas, neuroblastomas and melanomas (Lloyd, 1993). Their pattern of cell surface expression is altered during the process of the malignant transformation (Halcomori, 1985). More than 70 gangliosides have been identified although not all of these are found on tumours.

In terms of developing a vaccine, the induction of an effective immune response to carbohydrate antigens requires the co-presentation of carbohydrate epitopes (B epitopes) and T epitopes derived from protein to antigen presenting cells. This has traditionally been achieved by chemical conjugation of carbohydrate to carrier protein, the best known example being the *haemophilus influenzae* type b vaccines where a carbohydrate antigen is conjugated to either diphtheria toxoid, tetanus toxoid or *Neisseria meningitidis* major outer membrane protein. However, the use of chemical conjugation in the preparation of such vaccines presents inherent problems in that the structure of conformational epitopes may be altered thereby reducing or eliminating their antigenicity. In addition, chemical conjugation procedures are expensive, time consuming, very difficult to perform under uniform conditions and generally involve substantial losses of material. Further, in stimulating the immune response to such an antigen, adjuvants have commonly been used to increase immunogenicity of the antigen. One of the difficulties associated with the use of adjuvants stems from the unwanted reactivity which they may also induce.

Dose-site reactivities are a major concern for both veterinary and human use of adjuvant in vaccine preparation. One way of avoiding toxicity is via the use of immunostimulating complexes. Immunostimulating complexes are typically small, cage like structures 30 to 40 nanometers in diameter which retain their structure on freeze drying. The size can vary, however, depending on mode of preparation, composition and method used for measurement. The final formulation of a typical immunostimulating complex with an optimal amount of immunogenic protein or polypeptide is a weight ratio of saponin, cholesterol, phospholipids and protein or polypeptide (5:1:1:1). Such a typical immunostimulating complex is estimated to contain around 60% by weight saponin, around 10% each for cholesterol and phospholipids and the remainder protein or polypeptides. Proteins or polypeptides can be incorporated into the immunostimulating complex matrix either directly or by chemical coupling to a carrier protein (eg. influenza envelope protein) after incorporation of the carrier protein into the immunostimulating complex.

The saponin adjuvants, a group of surface active glycosides of plant origin, are highly effective adjuvants. However, although effective they nevertheless exhibit toxicity. Such toxicity is reducable by incorporation of saponin into an immunostimulating complex. This is due to the association of the saponin adjuvant with cholesterol in the complex thereby reducing its ability to bind to cholesterol in cell membranes. Further, a lesser amount of saponin is required to generate a similar level of adjuvant effect.

In work leading up to the present invention, the inventors have found that the phospholipid component of an immunostimulating complex can be replaced with ganglioside molecules since gangliosides are structurally related to phospholipids. Both molecules have two acyl chains joined through glycerol to a head group. Although not intending to limit the operations of the invention to any one mode of action, it is believed that because the nature of a ganglioside molecule is a fatty acid chain with a polar head group, the fatty acid chain immerses in the immunostimulating complex leaving the polar head group exposed, said head group thereby functioning as an exposed B cell epitope. Such a formulation can present the antigenic portion of the ganglioside at the surface of the immiunostimulating complex structure.

Accordingly, one aspect of the present invention relates to an immunogenic immunostimulating complex comprising a saponin preparation, a sterol, a protein epitope together with a phospholipid and at least one ganglioside or at least one ganglioside alone.

Saponin preparations, sterols and phospholipids suitable for use in the present invention are described in detail in PCT/AU95/00670, the disclosures of which are incorporated herein by reference.

An immunogenic immunostimulating complex in accordance with the present invention may be prepared by techniques which are well known to persons skilled in the art, and which are described in detail in the publications of Cox and Coulter, 1992 and Morein et al., Australian Patent Specifications No. 558258, 589915, 590904 and 632067 the disclosures of which are incorporated by reference herein. Since the preparation of the immunogenic immunostimulating complexes of the present invention does not involve chemical conjugation, the risk of altering the conformation of the ganglioside or protein epitope is minimized.

Multiple proteins and gangliosides can be incorporated into a single immunostimulating complex. This permits the preparation of immunostimulating complexes wherein the ratio of protein components to gangliosides varies between individual immunostimulating complexes.

Reference hereinafter to "gangliosides" should be read as including reference to all forms of gangliosides and derivatives thereof. Derivatives include fragments, parts, portions, chemical equivalents, mutants, homologs and analogs. Chemical equivalents of a ganglioside can act as a functional analogue of the ganglioside. Chemical equivalents may not necessarily be derived from a ganglioside but may share certain conformational similarities. Alternatively, chemical equivalents may be specifically designed to mimic certain physiochemical properties of the ganglioside. Chemical equivalents may be chemically synthesised or may be detected following, for example, natural product screenings.

Homologs of gangliosides contemplated herein include, but are not limited to, gangliosides derived from different species.

Preferably, said ganglioside is selected from GM2, GD2, GD3 and/or GT3 (Lloyd, 1993) or derivatives thereof.

Accordingly, in this preferred embodiment the present invention relates to an immunogenic immunostimulating complex comprising a saponin preparation, a sterol, a protein epitope together with a phospholipid and at least one of the gangliosides GM2, GD2, GD3 and/or GT3 or at least one of the gangliosides GM2, GD2, GD3 and/or GT3 alone.

The "protein" in the complex of said invention includes a T cell epitope suitable for presentation by an antigen presenting cell. Examples include but are not limited to the melanoma antigens e.g. Mel 40, MAGE, GAGE, ESO1, Melan A, Mage 3 (Stockert et al., 1998), influenza haemagglutinin, key hole limpet haemocyanin or cancer specific proteins (e.g. cancer specific proteins which are relevant to the cancer in respect of which the therapeutic vaccine will be used) their functional derivatives, chemical equivalents, homologs, analogs, mutants, variants or derivatives thereof. Said protein may act as both a T cell epitope to help induce antibody responses to gangliosides and as a protective antigen in its own right. For example, Melan A can provide the T cell epitope suitable for presentation by an antigen presenting cell thereby assisting in the induction of an antibody response to the ganglioside component of the present invention but can also stimulate an immune response against the Melan A epitope, itself. Where said protein is a melanoma specific antigen, the induction of an immune response against said protein may yield therapeutic efficacy. In a particularly preferred embodiment, said proteins may function as protective antigens in their own right.

According to one preferred aspect of the present invention there is provided an immunogenic immunostimulating complex comprising a saponin preparation, a sterol, influenza haemagglutinin together with a phospholipid and at least one of the gangliosides GM2, GD2, GD3 and/or GT3 or at least one of the gangliosides GM2, GD2, GD3 and/or GT3 alone.

In another preferred aspect, said protein is a melanoma specific protein.

According to this preferred aspect of the present invention there is provided an immunogenic immunostimulating complex comprising a saponin preparation, a sterol, a melanoma specific protein together with a phospholipid and at least one of the gangliosides GM2, GD2, GD3 and/or GT3 or at least one of the gangliosides GM2, GD2, GD3 and/or GT3 alone.

The term "mammal" includes humans, primates, livestock animals (eg. horses, cattle, sheep, pigs, donkeys), laboratory test animals (eg. mice, rats, rabbits, guinea pigs), companion animals (eg. dogs, cats) and captive wild animals (eg. kangaroos, deer, foxes). Preferably, the mammal is a human or laboratory test animal. Even more preferably, the mammal is a human.

Most gangliosides in a cell are found in the plasma membrane, with the carbohydrate moiety pointing outwards. In light of both this and the fact that gangliosides are prevalent in tumours they are ideally suited to act as cell surface antigen targets. Further, several of the 70 plus gangliosides which have been identified are predominantly found on certain tumour cells. For example, melanoma tumours express varying amounts of GM2 and GD2. Further, the protein which is incorporated into the immunostimulating complex is a T cell epitope suitable for presentation by an antigen presenting cell. A further aspect of the present invention therefore relates to the use of the invention to induce an immune response in a mammal, including but not limited to a humoral and/or cell mediated immune response.

Accordingly, another aspect of the present invention relates to a vaccine composition comprising as the active component an immunogenic immunostimulating complex as broadly described above, together with one or more pharmaceutically acceptable carriers and/or diluents.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

A further aspect of the present invention relates to the use of the invention in relation to disease conditions. For example, the present invention is particularly useful, but in no way limited to use in treating tumours and in particular, melanomas.

Accordingly, another aspect of the present invention relates to a method of eliciting or inducing an immune response to a disease condition in a mammal said method comprising administering to said mammal an effective amount of a vaccine composition as hereinbefore described wherein eliciting or inducing said immune response inhibits, halts or delays the onset or progression of the disease condition.

An "effective amount" means an amount necessary at least partly to attain the desired immune response, or to delay the onset or inhibit progression or halt altogether, the onset or progression of a particular condition being treated. This amount varies depending upon the health and physical condition of the individual to be treated, the taxonomic group of individual to be treated, the capacity of the individual's immune system to synthesize antibodies, the degree of protection desired, the formulation of the vaccine, the assessment of the medical situation, and other relevant factors. It is expected that the amount will fall in a relatively broad range that can be determined through routine trials.

Preferably, said disease condition is a tumour and even more preferably melanoma.

According to this preferred aspect the invention relates to a method of eliciting or inducing an immune response to melanoma or other tumour in a mammal, said method comprising administering to said mammal an effective amount of a vaccine composition as hereinbefore described wherein eliciting or inducing said immune response inhibits, halts or delays the onset or progression of the melanoma or other tumour.

As described above, the mammal undergoing treatment may be human or an animal in need of therapeutic or prophylactic treatment of a disease condition or a potential disease condition.

In yet another aspect the present invention relates to the use of an immunogenic immunostimulating complex in the manufacture of a medicament for inhibiting, halting or delaying the onset or progression of a disease condition.

Preferably said disease condition is a tumour and even more preferably a melanoma.

Yet another aspect of the present invention relates to an agent for use in inhibiting, halting or delaying the onset or progression of a disease condition said agent comprising an immunogenic immunostimulating complex.

Preferably said disease condition is a tumour and even more preferably a melanoma.

Further features of the present invention are more fully described in the following Figures and/or Examples. It is to be understood, however, that this detailed description is included solely for the purposes of exemplifying the present invention. It should not be understood in anyway as a restriction on the broad description of the invention as set out above.

EXAMPLE 1

Preparation of Immunostimulating Complexes Containing Monosialoganglioside GM2 and Influenza Proteins Immunostimulating complex formulations were prepared by the method of Morein et al. (1989). Briefly, to 5.3 mg of detergent disrupted haemagglutinin (HA) from the human A/Texas strain in 4.5 ml PBS was added 1 ml of a solution containing 10 mg/ml cholesterol in 20% MEGA-10 detergent (w/v) and 1 ml of an aqueous solution containing 10 mg/ml monosialoganglioside GM2 (Larodan Fine Chemicals AB, Sweden). Following mixing, 3.5 ml of a solution containing 10 mg/ml ISCOPREP™703 in PBS was added, the solution was held at 25° C. for 1 hour with gentle mixing. During subsequent dialysis against PBS/azide immunostimulating complexes containing influenza HA, cholesterol, ISCOPREP™703 and monosialoganglioside GM2 are formed. These immunostimulating complexes were of typical appearance by electron microscopy. Similarly, A/Texas immunostimulating complexes were prepared where the monosialoganglioside GM2 was replaced with dipalmitoyl phosphatidyl choline (DPPC).

Figure 1:
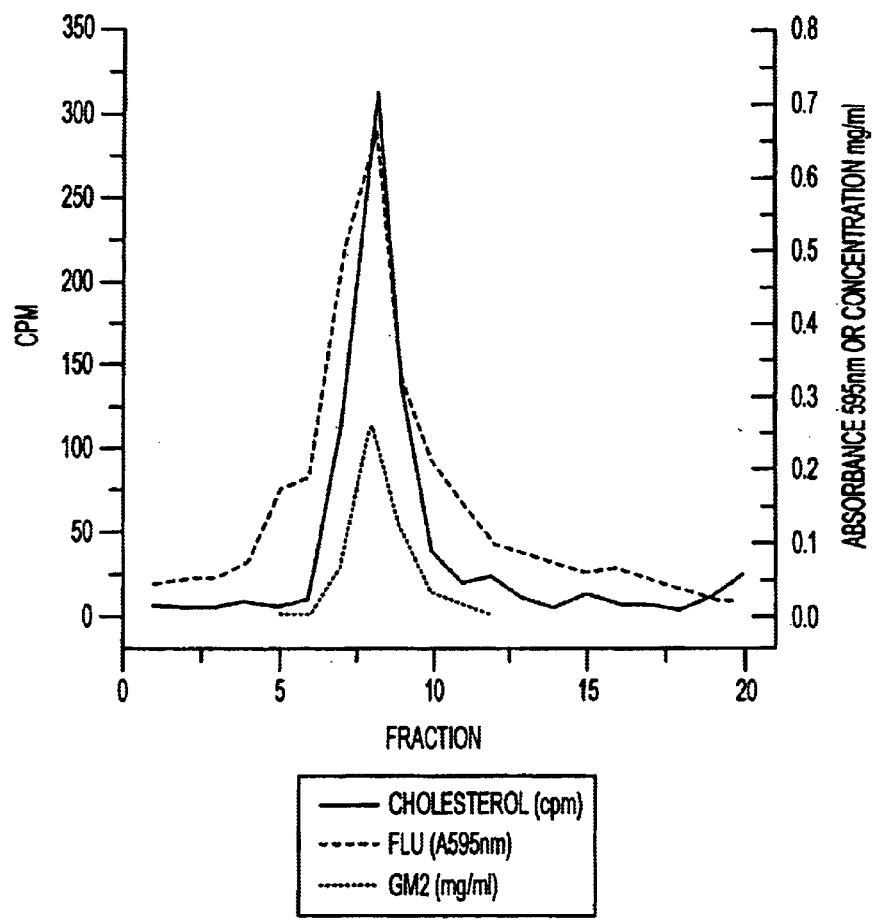
FIG. 1 is a graphical representation of the sucrose gradient analysis of GM2 A/Texas immunostimulating complex indicating the cholesterol, protein and GM2 monosialoganglioside contents of sucrose gradient fractions.

After dialysis, preparations were purified on a sucrose gradient (10 to 50% sucrose) and fractions analysed for radioactivity (to detect tritiated cholesterol), protein (to detect influenza antigens) and by HPLC (to detect monosialoganglioside GM2) (FIG. 1). The detection of monosialoganglioside GM2 using reverse phase HPLC was according to Palestini et al. (1990). All three basic components peaked in those fractions in which typical immunostimulating complexes were identified by EM, indicating incorporation of all components into the immunostimulating complex.

EXAMPLE 2

Immunization of Mice with A/Texas Immunostimulating Complexes Containing Monosialoganglioside GM2 or DPPC Ten outbred NIH strain mice were immunized subcutaneously on day 0, day 28 and day 110 with 0.1 ml of GM2 A/Texas immunostimulating complex (preparation described in Example 1) containing 11 μg ISCOPREP™703, 1 μg the influenza protein from the human A/Texas strain and 3 μg monosialoganglioside GM2. All mice were retroorbitally bled on day 28, 35 and 125.

Induction of serum IgG antibodies directed against A/Texas were measured by Enzyme Immuno Assay (EIA). F96 MaxiSorp plates (Nunc, Denmark) were coated with 2.5 μg/well of disrupted A/Texas influenza virus in 0.05 M carbonate buffer, pH 9.6 over night at room temperature. The plates were blocked in 0.01 M PBS, pH 7.2 containing 0.1% casein, 0.01% Thiomersal and stabiliser for a minimum of 1 hour at room temperature and were dried under vacuum. Fivefold dilutions of mouse sera, starting from 1 in 1000, were made in 0.01 M PBS, pH 7.2 containing 1% Casein, 0.05% Tween-20 and 0.01% Thiomersal (assay buffer) and 100 μl/well was incubated for 2 hours at room temperature. Each plate included a standard serum diluted twofold starting from 1 in 20. After five washings in 0.01 M PBS, pH 7.2 containing 0.05% Tween-20 and 0.0005% Thiomersal the plates were incubated for 2 hours at room temperature with horse-radish peroxidase conjugated goat anti mouse IgG (Kirkegaard & Perry Laboratories, USA) diluted to 0.06 μg/ml in assay buffer. After three additional washes substrate solution (TMB, Microwell Peroxidase Substrate System, Kirkegaard & Perry Laboratories, USA) was added at 100 μl/well and incubated for 10 minutes at room temperature. The enzyme reaction was stopped by addition of 50 μl/well of 0.5 M $H_2SO_4$ and the absorbance at 450 nm was read. End-point titres were calculated from a four parameter fit analysis of the linear part of the standard curve.

Figure 2:
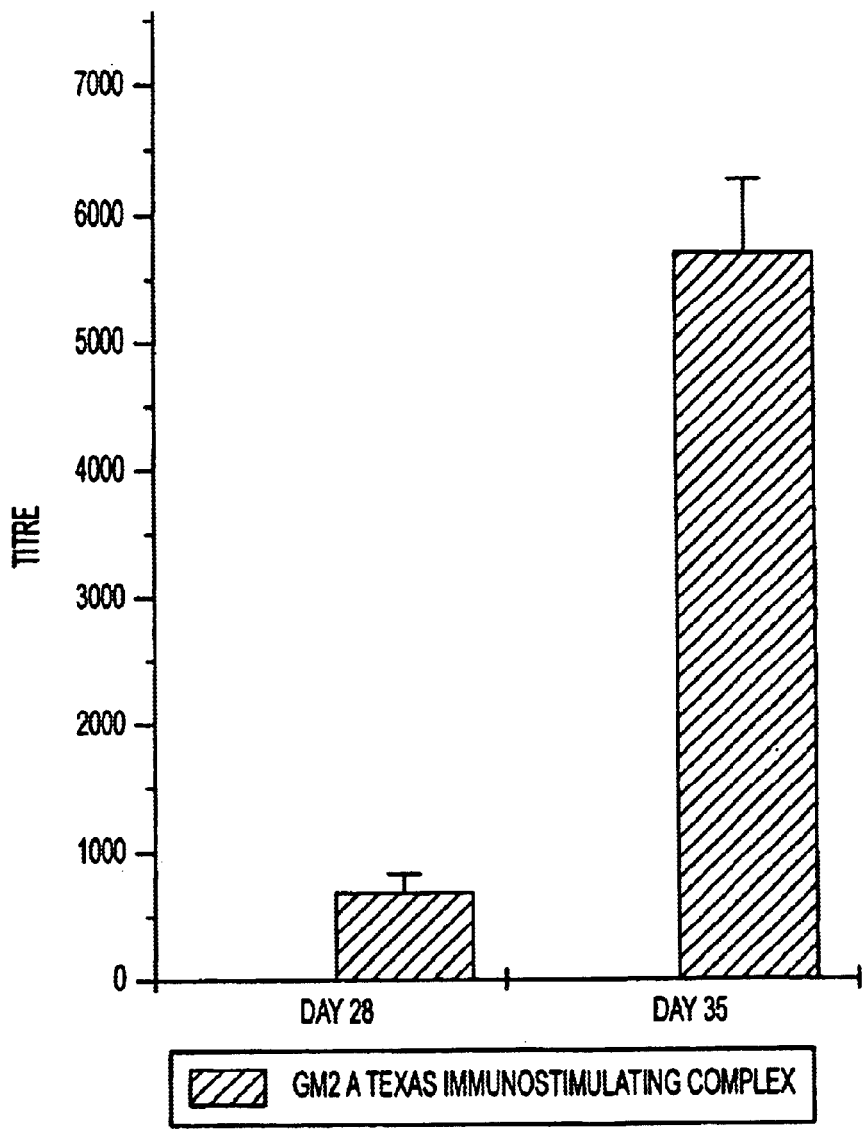
FIG. 2 is a graphical representation of serum antibody response to a A/Texas. Mean titres +/− SEM are shown after first and second immunisation of mice with A/Texas immunostimulating complexes or A/Texas Immunostimulating complexes containing monosialoganglioside GM2.

Immunization with GM2 A/Texas immunostimulating complex gave rise to IgG antibodies directed against A/Texas (FIG. 2). A significant booster effect was seen between the first and the second immunization (p<0.05). Titres were compared by the Wilcoxon signed rank test and the Mann-Whitney U-test using the GraphPad Instat v2.03 computer software.

Induction of serum antibodies to monosialoganglioside GM2 were measured in a dot blot assay using immunostimulating complex containing monosialoganglioside GM2 (from Larodan Fine Chemicals AB, Sweden) but no protein as coating material (1.7 μg/dot ISCOPREP™703 and 0.25 μg/dot GM2). Preparation of the GM2 immunostimulating complex was essentially the same as for the GM2 A/Texas immunostimulating complex in Example 1, omitting the addition of the influenza protein. Dots containing ISCOMATRIX™ were used as control material (1.7 μg/dot ISCOPREP™703). Preparation of ISCOMATRIX™ was essentially the same as for the GM2 A/Texas immunostimulating complex in Example 1, omitting the addition of the influenza protein and replacing the monosialoganglioside GM2 with DPPC. Dots containing purified and disrupted A/Texas were used as additional control material (approximately 80 ng/dot of haemagglutinin). Dots were made on nitro cellulose sheets (0.5–1 μl/dot). After drying for 10 minutes at room temperature the nitro cellulose sheets were incubated for 1 hour at room temperature in 0.01 M PBS, pH 7.2 containing 3% Bovine Serum Albumin (BSA) (blocking buffer). Blots were incubated with a pool of sera taken on day 125 from mice immunized with GM2 A/Texas immunostimulating complex, a pool of sera from mice immunized with A/Texas immunostimulating complex and sera from naive mice. The three pools of sera were all diluted 1 in 1000 in blocking buffer added to the blots and incubated for 1 hour at room temperature. After washing three times, each for 10 minutes in 0.01 M PBS, pH 7.2 containing 0.3% BSA the blots were incubated with horse-radish peroxidase conjugated goat anti mouse IgG γ specific (Kirkegaard & Perry Laboratories, USA) diluted to 0.06 μg/ml in blocking buffer for 1 hour at room temperature. After three further washings, substrate solution (4CN Peroxidase Substrate System, Kirkegaard & Perry Laboratories, USA) was added and incubated for approximately 10 minutes at room temperature. The blots were dried and stored in a dark place.

GM2-immunostimulating complex was recognized by sera from the mice immunized with GM2 A/Texas immunostimulating complex but not by control sera raised against A/Texas-immunostimulating complex (Table 1) indicating that a population of antibodies in the sera are directed against GM2. Sera from the mice immunized with GM2 A/Texas immunostimulating complex also reacted with ISCOMATRIX™ not containing GM2. The control sera raised against A/Texas-immunostimulating complex did not react with ISCOMATRIX™. It is probable that the mice immunized with GM2 A/Texas immunostimulating complex produce some antibodies recognising the galactose moiety, which is a consistent carbohydrate at the C3 position of the aglycone quillaic acid on most, if not all, quillaia saponins.

EXAMPLE, 3

Immunization OF Rabbits with A/Texas Immunostimulating Complexes Containing Monosialoganglioside GM2

Three rabbits were immunized subcutaneously on day 0 and day 19 with 0.5 ml of GM2 A/Texas immunostimulating complex (preparation described in Example 1) containing 200 μg ISCOPREP™703, 20 μg A/Texas and 50 μg monosialoganglioside GM2. The rabbits were bled on day 0, day 7, day 19 and day 25.

Induction of serum IgG antibodies directed against A/Texas were measured by EIA. The assay was essentially the same as the EIA procedure described in Example 2 with the exception that a horse-radish peroxidase conjugated goat anti rabbit IgG H+L (Kirkegaard & Perry Laboratories, USA) diluted to 1 μg/ml in assay buffer were used instead of the mouse conjugate.

Figure 3:
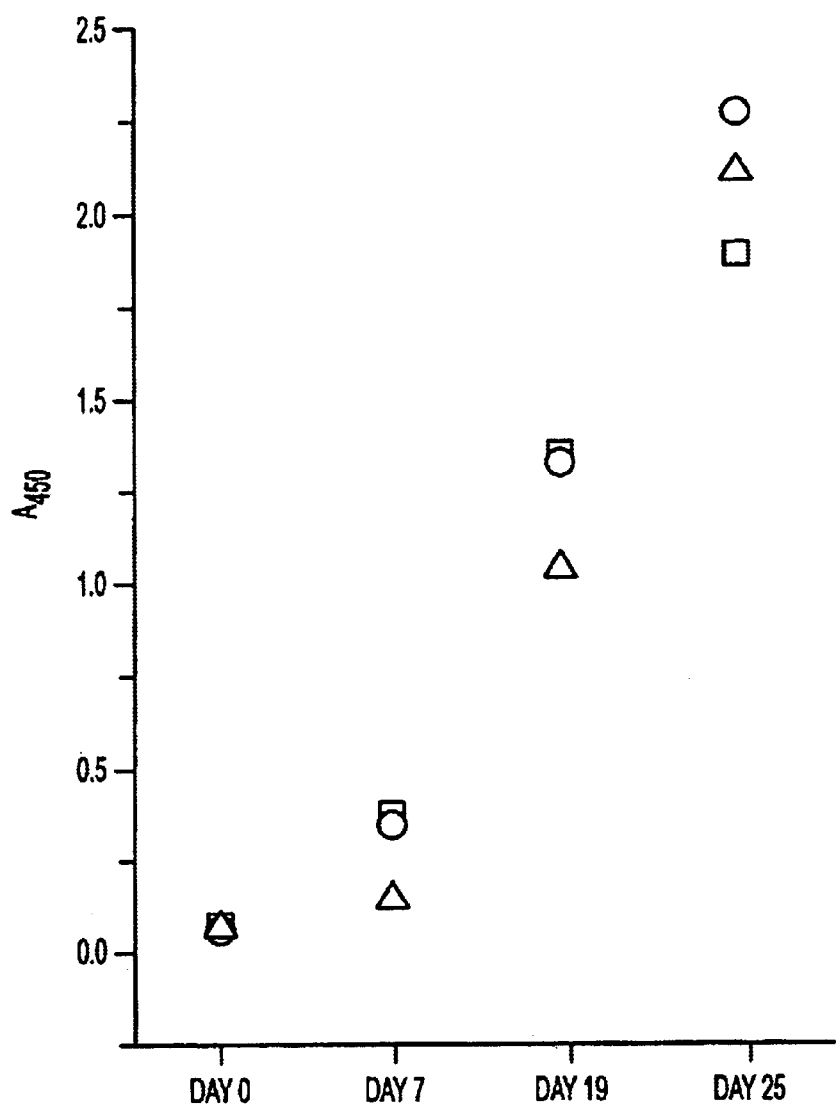
FIG. 3 is a graphical representation of individual serum antibody levels to A/Texas of three rabbits immunised with GM2 A/Texas immunostimulating complex. Antibody levels are shown as the absorbence of sera diluted 1:6250.

As shown in FIG. 3 antibody levels against A/Texas influenza proteins were raised after immunization with GM2 A/Texas immunostimulating complex. After the first immunisation the antibody levels increased approximately four fold from day 0 to day 7 followed by another approximate four fold rise from day 7 to day 19 (p=0.05). A significant booster effect was seen between first and second immunization (p=0.05) and the antibody levels increased about 1.5 times. Antibody levels were compared by the Wilcoxon signed rank test using GraphPad Instat v2.03 computer software.

Induction of serum IgG antibodies directed against monosialoganglioside GM2 were measured by EIA. F96 MaxiSorp plates (Nunc, Denmark) were coated with monosialoganglioside GM2 (Larodan Fine Chemicals AB, Sweden) dissolved in 0.1 M Carbonate buffer, pH 9.4 at 0.1 μg/well. The plates were incubated over night at +4° C. and the following steps were essentially the same as the EIA procedure described in Example 2 with the exception that a horse-radish peroxidase conjugated goat anti rabbit IgG (Kirkegaard & Perry Laboratories, USA) diluted to 1 μg/ml in assay buffer was used instead of the mouse conjugate.

Figure 4:
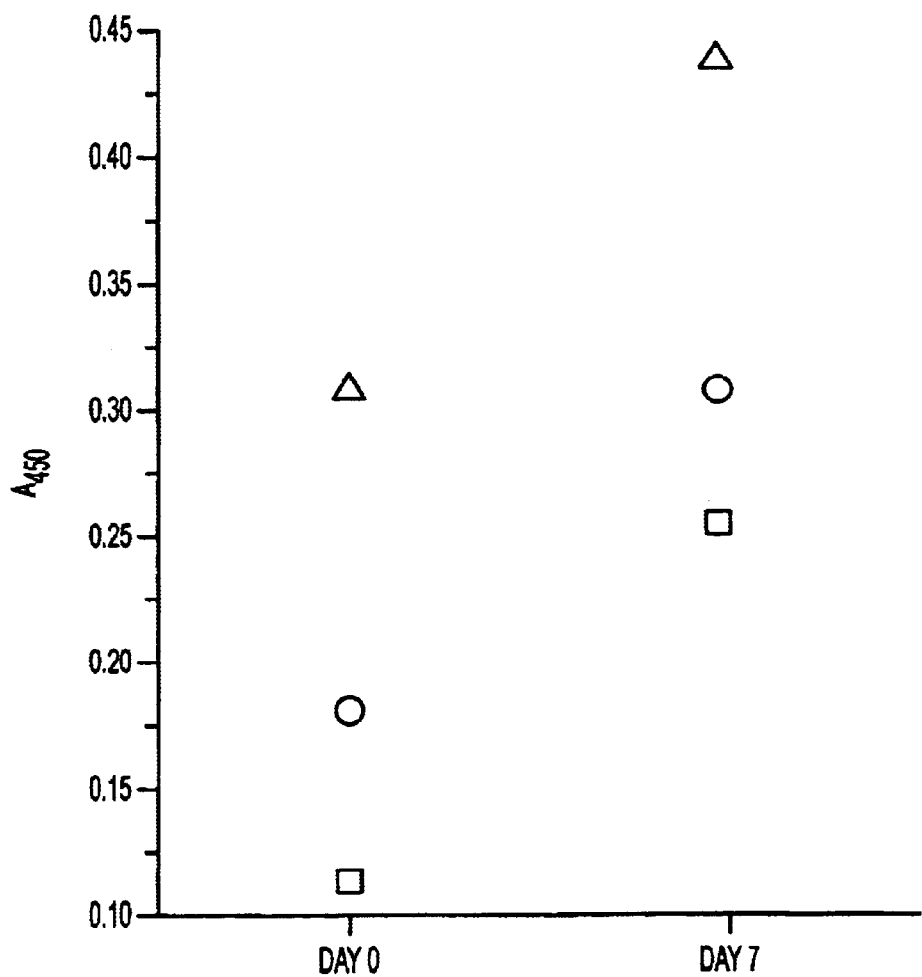
FIG. 4 is a graphical representation of individual serum antibody levels to monoganglioside GM2 of three rabbits immunised with GM2 A/Texas immunostimulating complex. Antibody levels are shown as the absorbence of sera diluted 1:25.

FIG. 4 shows that the individual antibody levels to monosialoganglioside GM2 were approximately 2 times higher on day 7 than on day 0 for all rabbits indicating that low levels of antibodies against monosialoganglioside GM2 were produced.

Induction of serum IgG antibodies directed against monosialoganglioside GM2 were also measured using a dot blot assay. The method was essentially the same as the procedure described in Example 2 with the exception that a horse-radish peroxidase conjugated goat anti rabbit IgG (Kirkegaard & Perry Laboratories, USA) diluted to 1 μg/ml in assay buffer was used instead of the mouse conjugate.

GM2-immunostimulating complex was only recognized by rabbit sera taken 1 week after the second immunization (day 25) indicating that a booster response to antibodies directed against monosialoganglioside GM2 was seen (Table 2). The EIA appears to have higher sensitivity than the dot blot assay as a response was detected on day 7. Analogous to Example 2 the rabbit sera from day 25 also reacted with ISCOMATRIX™ not containing GM2. The earlier bleeds did not react with ISCOMATRIX™. It is probable that also the rabbits immunized with GM2 A/Texas immunostimulating complex produce some antibodies recognising the galactose moiety probably present on the aglycone quillaic acid in the ISCOMATRIX™.

EXAMPLE 4

Preparation of Immunostimulating Complexes Containing Disialoganglioside GD3 and Palmitifted Ovalbumin Immunostimulating complex containing disialoganglioside GD3 and palmitified ovalbumin (p-OVA) was essentially prepared according to the method described in Example 1 and in Mowat et al. (1991). The monosialoganglioside GM2 was replaced with disialoganglioside GD3 and A/Texas with p-OVA.

Figure 5:
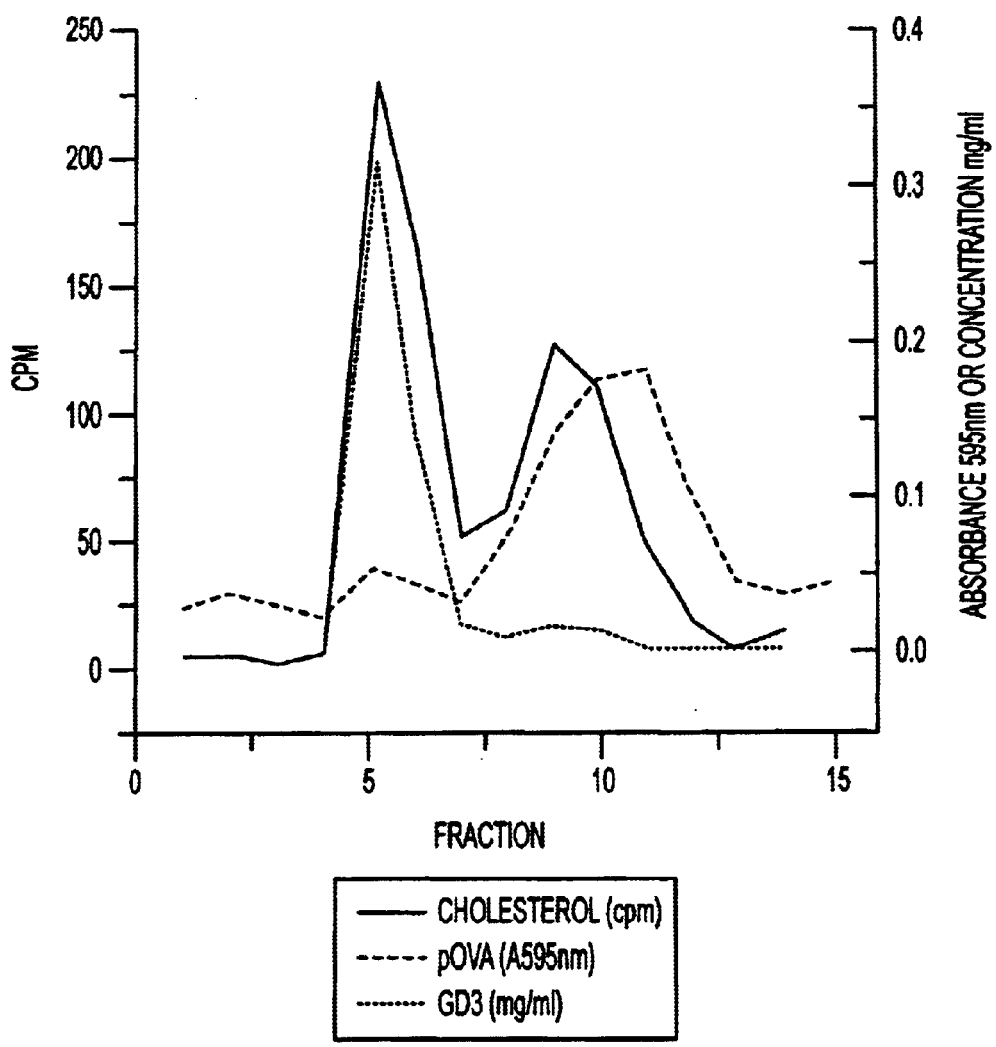
FIG. 5 is a graphical representation of the sucrose gradient analysis of GD3 p-OVA immunostimulating complex indicating the cholesterol, protein and GD3 monosialoganglioside contents of sucrose gradient fractions.

After dialysis, preparations were purified on a sucrose gradient (10 to 50% sucrose) and fractions analysed for radioactivity (to detect tritiated cholesterol), protein (to detect p-OVA) and by HPLC (to detect disialoganglioside GD3) (FIG. 5). The detection of disialoganglioside GD3 using reverse phase HPLC was according to Palestini et al. (1990). All three basic components peaked in those fractions in which typical immunostimulating complexes were identified by EM, indicating incorporation of all components into the immunostimulating complex.

EXAMPLE 5

Immunization of Rabbits with P-OVA Immunostimulating Complexes Containing Disialoganglioside GD3

Three rabbits were immunized subcutaneously on day 0 with 0.5 ml of GD3 p-OVA immunostimulating complex (preparation described in Example 4) containing 200 μg ISCOPREP™703, 17 μg p-OVA and 111 μg disialoganglioside GD3. The rabbits were bled on day 0 and day 7.

Induction of serum IgG antibodies directed against ovalbumin were measured by EIA. F96 MaxiSorp plates (Nunc, Denmark) were coated with ovalbumin (Sigma, USA) dissolved in 10 mM Acetate buffer, pH 4.2 at 5 μg/well. The plates were incubated over night at +4° C. and the following steps were essentially the same as the EIA procedure described in Example 2 with the exception that a horse-radish peroxidase conjugated goat anti rabbit IgG H+L (Kirkegaard & Perry Laboratories, USA) diluted to 1 μg/ml in assay buffer were used instead of the mouse conjugate.

Figure 6:
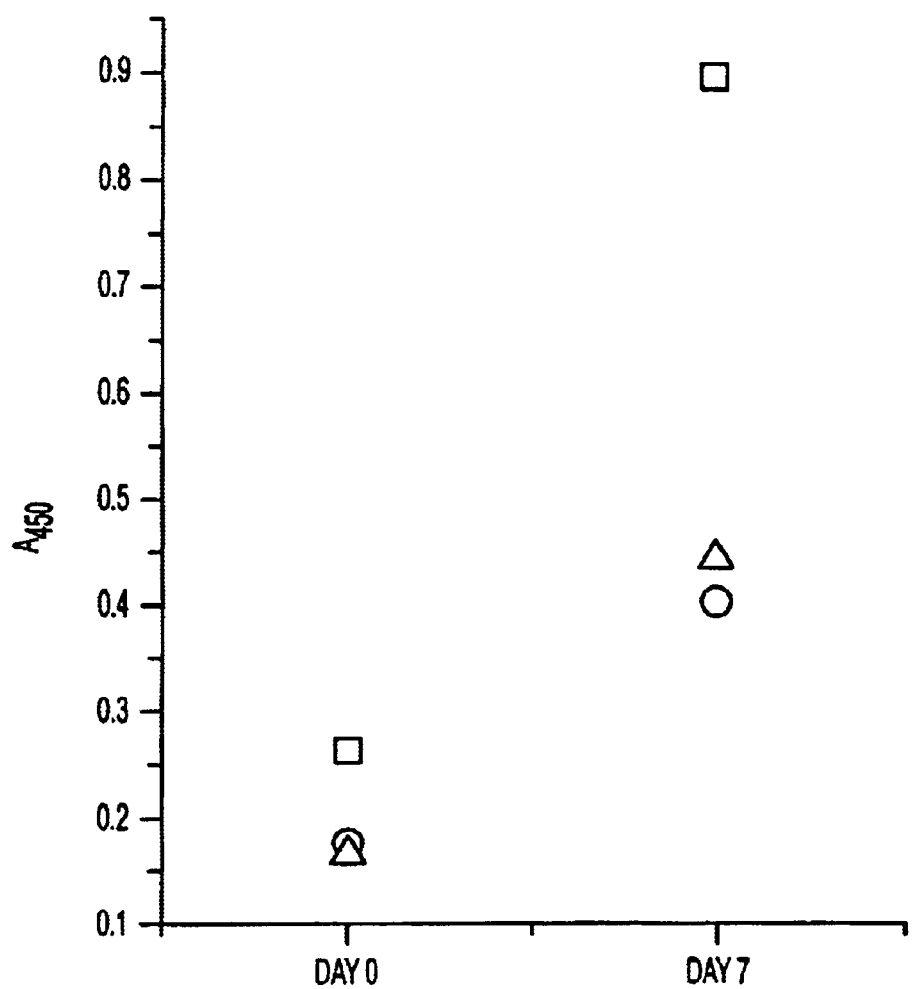
FIG. 6 is a graphical representation of individual serum antibody levels of ovalbumin of three rabbits immunised with GD3 p-OVA immunostimulating complex. Antibody levels are shown as the absorbence of sera diluted 1:640.

As shown in FIG. 6 antibody levels against ovalbumin were raised after immunization with GD3 p-OVA immunostimulating complex. The antibody levels increased approximately three fold from day 0 to day 7 (p=0.05). Antibody levels were compared by the Wilcoxon signed rank test using GraphPad Instat v2.03 computer software.

Induction of serum IgG antibodies directed against disialoganglioside GD3 were measured by EIA. F96 MaxiSorp plates (Nunc, Denmark) were coated with disialoganglioside GD3 (Larodan Fine Chemicals AB, Sweden) dissolved in 0.1 M PBS, pH 7.2 at 0.1 μg/well. The plates were incubated over night at +4° C. and the following steps were essentially the same as the EIA procedure described in Example 2 with the exceptions that Tween-20 was omitted in washing buffer and assay buffer and that a horse-radish peroxidase conjugated goat anti rabbit IgG (Kirkegaard & Perry Laboratories, USA) diluted to 1 μg/ml in assay buffer was used instead of the mouse conjugate.

Figure 7:
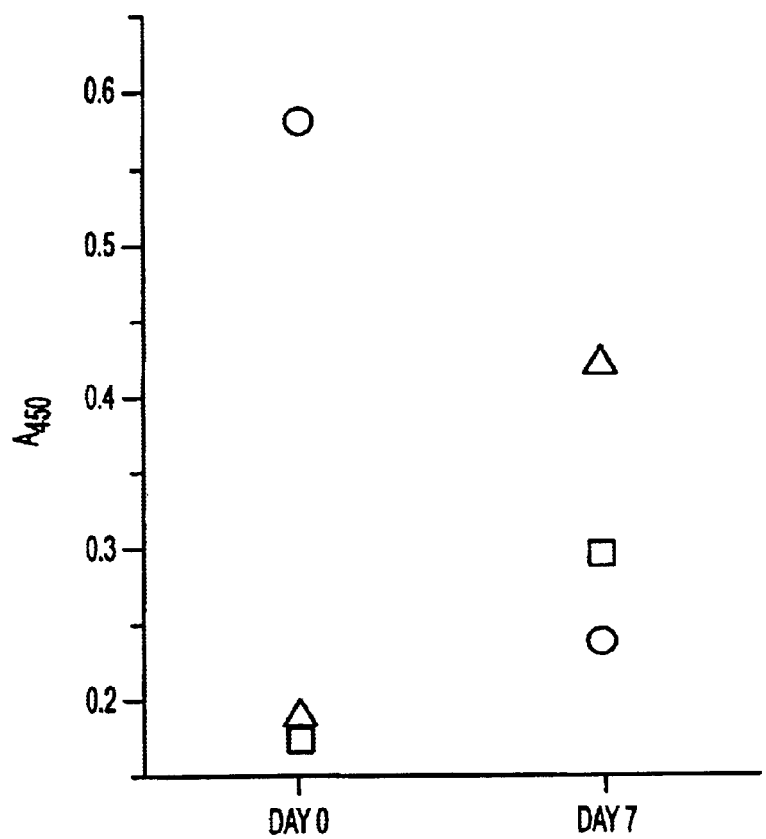
FIG. 7 is a graphical representation of individual antibody levels to monosialoganglioside GD3 of three rabbits immunised with GD3 p-OVA immunostimulating complex. Antibody levels are shown as the absorbence of sera diluted 1:40.

FIG. 7 shows that individual antibody levels to disialoganglioside GD3 increased approximately 1.5 times from day 7 to day 0 for 2 rabbits out of 3 indicating that low levels of antibodies against disialoganglioside GD3 were produced. The rabbit that did not respond had a high reading on day 0 which was reduced after immunisation.

ISCOPREP™703 and ISCOMATRIX™ are products of Iscotec A.B.—refer International Patent Application No. PCT/AU95/00670.

TABLE 1

Serum antibody response to monosialoganglioside GM2 measured by dot blot assay. Mice were immunized with GM2 A/Texas immunostimulating complex.

| | Detection with sera | | |
|---|---|---|---|
| Antigen in dot | α GM2 ATexas-immunostimulating complex | α A/Texas-immunostimulating complex | Neg. Mouse Sera |
| ISCOMATRIX ™ | + | – | – |
| GM2-immunostimulating complex | ++ | – | – |
| A/Texas | + | + | – |

– no reaction between antigen and sera
+ clear reaction between antigen and sera
++ strong reaction between antigen and sera

TABLE 2

Serum antibody response to monosialoganglioside GM2 measured by dot blot assay. Rabbits were immunized with GM2 A/Texas immunostimulating complex.

| | Detection with sera from rabbits immunised with GM2 A/Texas immunostimulating complex | | | |
|---|---|---|---|---|
| Antigen in dot | day 0 | day 7 | day 19 | day 25 |
| ISCOMATRIX ™ | – | – | – | + |
| GM2-immunostimulating complex | – | – | – | ++ |
| A/Texas | – | ++ | ++ | ++ |

– no reaction between antigen and sera
+ clear reaction between antigen and sera
++ strong reaction between antigen and sera

BIBLIOGRAPHY

Balch, C. M., Smalley, R. V., Bartolucci, A. A. *Cancer* 49:1079–1084, 1982.

Coit, D. G., Rogatko, A., Brennan, M. F. *Ann. Surg.* 214:627–636, 1991.

Cox, J. C. and Coulter, A. R. *Advances in Adjuvant Technology and Application in Animal Parasite Control Utilising Biotechnology* Chapter 4 Editor Yong, W. K. CRC Press, 1992.

Hakomori, S. I. *Cancer Res.* 45:2405–2414, 1985.

Lloyd, K. O. N.Y. *Acad. Sci.* 690:50–58, 1993.

Morein, B., Lougren, K., Hoglund, S. *Vaccines: Recent Trends and Progress. Nato ASI Series A: Life Sciences* Vol. 215, Editors Gregoriadis, G., Allison, A. C., and Poste, G., Plenum Press, p153, 1989.

Palestini et al. *J. Neurochem.* 54:230–235, 1990.

Ritter et al., *Cancer Res.* 50:1403–1410, 1990.

Stockert et al., *J. Exp. Med.* 187:1349–1354, 1998.

What is claimed is:

1. An immunostimulating complex comprising (i) a purified polypeptide capable of presentation by an antigen presenting cell, (ii) sterol, (iii) an unconjugated ganglioside selected from the group consisting of GM2, GD2, GD3, and GT3, and (iv) a saponin, which complex induces an immune response against the carbohydrate moiety of the ganglioside.

2. The immunostimulating complex of claim 1, wherein said polypeptide is further capable of stimulating an immune response against itself.

3. The immunostimulating complex of claim 1, wherein said selected from the group consisting of MEL 40, MAGE-3, ESO1, and melan A.

4. The immunostimulating complex of claim 1, wherein said polypeptide is an influenza haemagglutinin.

5. An agent for eliciting or inducing an immune response in a mammal having an astrocytoma, a neuroblastoma, or a melanoma, comprising as the active component an immunostimulating complex, or a composition thereof, of any one of claims 3, 5, 6, and 1.

6. An agent according to claim 5, wherein said mammal has a melanoma.

7. A composition comprising (i) the immunostimulating complex of claim 1, and (ii) a pharmaceutically acceptable carrier and/or diluent.

8. A method of eliciting or inducing an immune response in a mammal, said method comprising administering to said mammal an effective amount of the composition of claim 7 to elicit or induce said immune response.

9. The method of claim 8, wherein said mammal has a melanoma.

10. The method of claim 8, wherein said mammal is human.

* * * * *